(12) United States Patent
Su et al.

(10) Patent No.: US 8,597,481 B2
(45) Date of Patent: Dec. 3, 2013

(54) GAS SENSOR ELEMENT AND GAS SENSOR EQUIPPED WITH THE SAME

(75) Inventors: Zhenzhou Su, Okazaki (JP); Kiyomi Kobayashi, Kuwana (JP)

(73) Assignee: Denso Corporation, Kariya (JP)

( * ) Notice: Subject to any disclaimer, the term of this patent is extended or adjusted under 35 U.S.C. 154(b) by 195 days.

(21) Appl. No.: 13/106,979

(22) Filed: May 13, 2011

(65) Prior Publication Data

US 2011/0278169 A1    Nov. 17, 2011

(30) Foreign Application Priority Data

May 13, 2010  (JP) ................................. 2010-110780

(51) Int. Cl.
*G01N 27/407*   (2006.01)
*G01N 27/26*    (2006.01)

(52) U.S. Cl.
USPC ........... 204/429; 204/408; 204/410; 73/23.32

(58) Field of Classification Search
USPC ................. 204/421–431, 410, 411; 73/23.31, 73/23.32; 205/781, 783.5–785, 787
See application file for complete search history.

(56) References Cited

U.S. PATENT DOCUMENTS

| | | | | |
|---|---|---|---|---|
| 5,160,598 A | * | 11/1992 | Sawada et al. | 204/429 |
| 5,538,612 A | * | 7/1996 | Kojima et al. | 204/429 |
| 6,660,145 B2 | | 12/2003 | Hotta et al. | |
| 2002/0060152 A1 | * | 5/2002 | Hotta et al. | 204/429 |
| 2010/0163411 A1 | * | 7/2010 | Su et al. | 204/408 |

FOREIGN PATENT DOCUMENTS

| | | |
|---|---|---|
| JP | H01-203963 | 8/1989 |
| JP | 2002-181769 | 6/2002 |
| JP | 2006-038496 | 2/2006 |

OTHER PUBLICATIONS

Japanese Office Acton dated Apr. 24, 2012, issued in corresponding Japanese Application No. 2010-110780, with English translation.
Chinese Office Action issued for corresponding Chinese Patent Application No. 201110128522.6 dated Mar. 5, 2013 with English translation (16 pages).

* cited by examiner

*Primary Examiner* — J. Christopher Ball
*Assistant Examiner* — Jennifer Dieterle
(74) *Attorney, Agent, or Firm* — Nixon & Vanderhye P.C.

(57) ABSTRACT

A gas sensor element with a bottom part is composed of at least a solid electrolyte body of oxygen ion conductivity, a reference electrode, a detection electrode, an electrode protection layer which supports noble metal catalyst, and a heater. The electrode protection layer is composed of a covering layer, a catalyst layer and a poisoning layer. A quantity of the noble metal catalyst supported in the electrode protection layer at the bottom part of the gas sensor element is larger than that in the electrode protection layer at a leg part of the gas sensor. The bottom part of the gas sensor element has a high temperature rising speed more than the leg part when the heater generates heat energy.

6 Claims, 9 Drawing Sheets

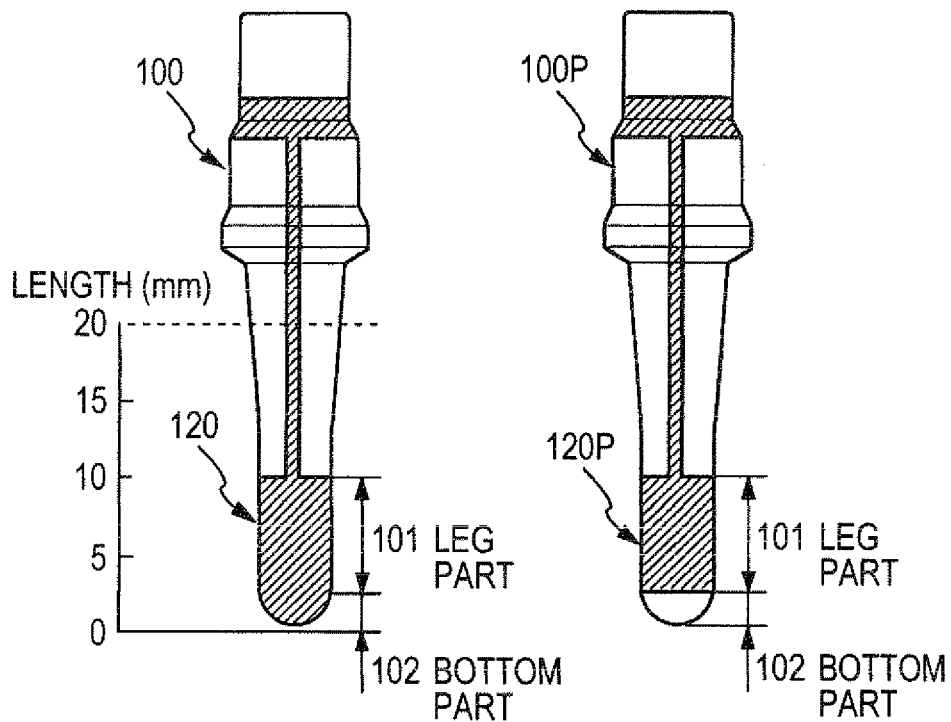
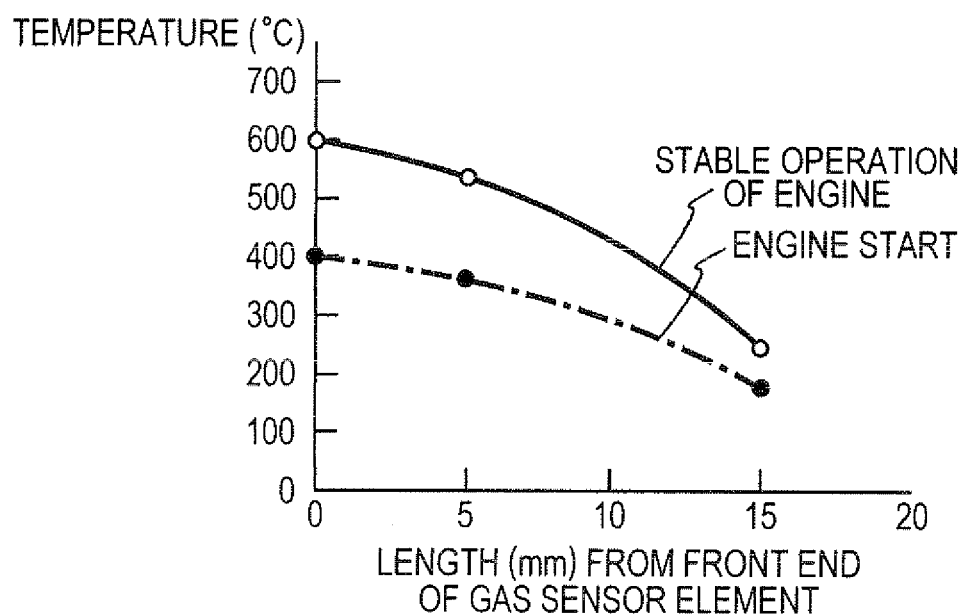

FIG. 9A   λ 0.9995 ⇔ 1.0005
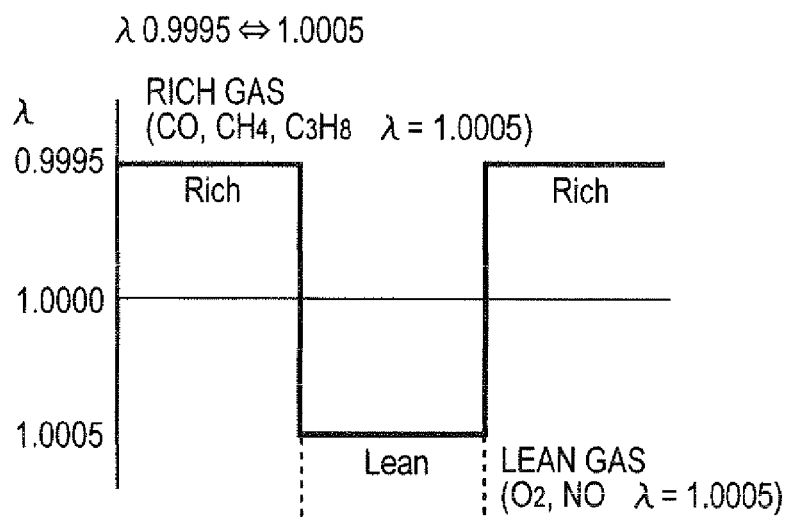
FIG. 9B
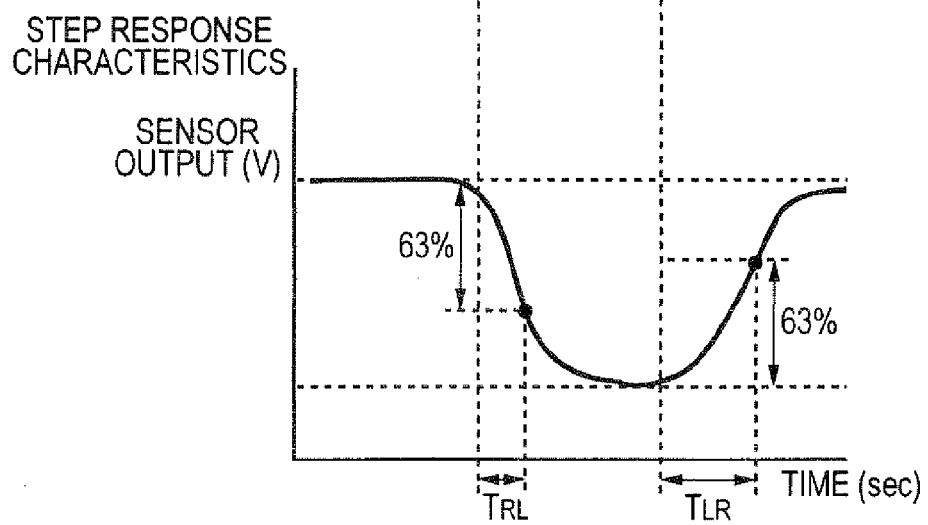
EVALUATION ON THE BASIS OF AVERAGE VALUE
BETWEEN OF 63% RESPONSE $T_{RL}$, $T_{LR}$

GAS SENSOR ELEMENT AND GAS SENSOR EQUIPPED WITH THE SAME

CROSS-REFERENCE TO RELATED APPLICATION

This application is related to and claims priority from Japanese Patent Application No. 2010-110780 filed on May 13, 2010, the contents of which are hereby incorporated by reference.

BACKGROUND OF THE INVENTION

1. Field of the Invention

The present invention relates to gas sensor elements capable of detecting a concentration of a specific gas component contained in a target detection gas such as exhaust gas emitted from an internal combustion engine, and relates to gas sensors equipped with the gas sensor element.

2. Description of the Related Art

For example, a conventional gas sensor is equipped with a gas sensor element. For example, Japanese patent laid open publication No. JP 2006-38496 has disclosed such a conventional gas sensor. The gas sensor element in the gas sensor is comprised of a solid electrolyte body, a detection electrode, a reference electrode, an electrode protection porous layer, and an anti-poisoning porous layer. The solid electrolyte body has oxygen ion conductivity. The detection electrode is formed on one surface of the solid electrolyte body and is in contact with a target detection gas. The reference electrode is formed on the other surface of the solid electrolyte body and is in contact with a reference gas. The detection electrode is covered with the electrode protection porous layer. The electrode protection porous layer supports catalyst metal particles. The electrode protection porous layer is covered with the anti-poisoning porous layer. The anti-poisoning porous layer protects the catalyst metal particles from poisoning.

The conventional gas sensor having the above structure can be used as a gas sensor which detects a concentration of oxygen or nitrogen oxide NOx contained in exhaust gas emitted from an internal combustion engine of a motor vehicle. During the beginning of engine start, the exhaust gas contains a large quantity of hydrogen. In general, hydrogen moves at high speed through the electrode protection layer in the gas sensor element compared to other gas components such as oxygen contained in the target detection gas. Accordingly, because such hydrogen reaches and reacts to the detection electrode before other gas components reach the detection electrode, the gas sensor often causes error detection, and detects an incorrect $\lambda$-point which is shifted from a true $\lambda$ point. That is, the conventional gas sensor has a possibility of causing a $\lambda$-shift.

In order to avoid such a $\lambda$-shift problem, the conventional gas sensor, for example, disclosed in Japanese patent laid open publication No. JP2006-38496, catalyst metal particles are supported on the electrode protection layer. This structure of the conventional gas sensor element forcedly places hydrogen contained in the target detection gas in reaction with the catalyst metal particles supported on the electrode protection layer, and this structure prevents hydrogen from reaching the detection electrode.

By the way, there is a cup-shaped gas sensor having the above characteristics is comprised of a leg part, as the solid electrolyte body, having a cylindrical shape extending along its axial direction, and a bottom part (or a closed base) with which the front of the leg part is closed. In such a cup-shaped gas sensor, a longitudinal shaped heater is inserted and placed in the inside of the solid electrolyte body. When receiving electric power, the longitudinal shaped heater generates heat energy in the gas sensor element, and the heat energy activates oxygen ion conductivity and catalyst layer reaction characteristics of the solid electrolyte body.

During the beginning of the engine start, exhaust gas as the target detection gas is hydrogen rich, and the bottom part at the front side of the gas sensor element has a high temperature rising speed when compared with the leg part. As a result, the gas sensor element has a temperature change distribution, and does not have a uniform temperature distribution.

Accordingly, during the beginning of the engine start, because the catalyst metal particle placed at the bottom part is rapidly activated, it is difficult to adequately suppress hydrogen from reaching the detection electrode. It is thereby difficult to avoid such a $\lambda$-shift problem.

In addition, because gas adsorbed in the catalyst is also increased and on the other hand the diffusion speed of the target detection gas is decreased when the quantity of catalyst supported on the catalyst layer in the electrode protection layer is increased, the response characteristics of the gas sensor element are often decreased.

SUMMARY OF THE INVENTION

It is an object of the present invention to provide a gas sensor equipped with a gas sensor element with superior response characteristics and less $\lambda$-shift problem.

To achieve the above purposes, the present invention provides a gas sensor element having a solid electrolyte body, a reference electrode, a detection electrode, an electrode protection layer, and a heater. The solid electrolyte body has ion conductivity characteristics. The solid electrolyte body has a cylindrical shape and a bottom part (or a closed base). The reference electrode is formed on an inner surface of the solid electrolyte body. The detection electrode is formed on an outer surface of the solid electrolyte body. The electrode protection layer covers the outer surface of the solid electrode body with the detection electrode, and supports noble metal catalyst. Through the electrode protection layer, a target detection gas passes. The heater is inserted and placed in the inside of the solid electrolyte body and generates heat energy when receiving electric power. In particular, a front part of the gas sensor element has a leg part and a bottom part. The leg part is formed in parallel to an axial direction of the gas sensor element. An outer profile of a cross section of the leg part has a straight line shape. This cross section of the leg part is perpendicular to the axial direction of the gas sensor. An outer profile of a cross section of the bottom part has a curved shape. The detection electrode is one of a full-surface electrode and a partial electrode. The full-surface electrode is formed on the entire of the outer surface of the solid electrolyte body. The partial electrode is formed on the leg part of and not formed on the bottom part of the outer surface of the solid electrolyte body. The bottom part of the electrode protection layer has a first temperature rising speed when the heater generates heat energy. The leg part of the electrode protection layer has a second temperature rising speed when the heater generates heat energy. The bottom part of the electrode protection layer having the first temperature rising speed has a first quantity of noble metal catalyst. The leg part of the electrode protection layer having the second temperature rising speed has a second quantity of noble metal catalyst. The first temperature rising speed is higher than the second temperature rising speed. The first quantity of noble metal catalyst is larger than the second quantity of the noble metal catalyst.

When the heater heats the solid electrolyte body of the gas sensor element immediately after the gas sensor starts to operate, the solid electrolyte body has a part having a high temperature rising speed and a part having a low temperature rising speed. That is, the solid electrolyte body has a temperature distribution. When the heater generates heat energy, the part such as the bottom part having the high temperature rising speed is rapidly activated. The part having the high temperature rising speed promotes the output of the gas sensor element more than the part having the low temperature rising speed such as the leg part.

On the other hand, when target detection gas to be detected is exhaust gas emitted from an internal combustion engine, the target gas contains hydrogen rich during the beginning of the engine start. Hydrogen contained in the exhaust gas has a high diffusion speed in the electrode protection layer of the gas sensor element. In general, there is a tendency to shift a λ-point of the gas sensor element toward a lean side when the engine starts. That is, the λ-point shift often occurs in the gas sensor element when the engine starts.

In order to solve the above problem, the gas sensor element as one aspect of the present invention has an improved structure in which the bottom part having the high temperature rising speed has a large quantity of noble metal catalyst. Accordingly, it is possible for the bottom part having the high temperature rising speed to adequately react to hydrogen contained in the target detection gas. This makes it possible to suppress the influence of hydrogen on the detection electrode.

In addition, because the leg part having a low temperature rising speed has a low quantity of noble metal catalyst, the noble metal catalyst adsorbs a less quantity of the target detection gas under the stable condition when the temperature of the entire of the gas sensor element is adequately increased and stable. Accordingly, because the diffusion speed of the target detection gas in the electrode protection layer does not decrease, it is possible for the gas sensor element according to the present invention to maintain a high response characteristic.

In the gas sensor element as another aspect of the present invention, at least one of the thickness of the electrode protection layer at a boundary part between the leg part and the bottom part and the thickness of the electrode protection layer in the bottom part is thicker than the thickness of the electrode protection layer in the leg part.

Further, in the gas sensor element as another aspect of the present invention, at least one of the supporting ratio of noble metal catalyst in the electrode protection layer at the boundary part between the leg part and the bottom part and the supporting ratio of noble metal catalyst in the electrode protection layer in the bottom part is larger than the supporting ratio of noble metal catalyst in the electrode protection layer in the leg part.

According to the present invention, the inner wall of the solid electrolyte body which faces the boundary part between the bottom part is close to the front end of the heater which is inserted in the inside of the solid electrolyte body. Accordingly, when compared with the temperature rising speed of the leg part, the boundary part between the leg part and the bottom part and/or the bottom part has a high temperature rising speed and has an increased quantity of noble metal catalyst which is to be activated. Therefore even if the gas sensor element is working in the exhaust gas containing a high concentration hydrogen, for example, during the beginning period of the engine start, it is possible for the noble metal catalyst in the electrode protection layer in the bottom part of the gas sensor element to adequately react to hydrogen, and to suppress hydrogen from reaching the detection electrode.

Further, according to the present invention, when the temperature of the entire of the gas sensor element is increased and the gas sensor element enters the stable condition, because the electrode protection layer in the leg part of the gas sensor element contains a low concentration of noble metal catalyst, the noble metal catalyst adsorbs a less amount of the target detection gas, and the diffusion speed of the target detection gas is not thereby decreased. This makes it possible for the gas sensor element to have a high response characteristic. The present invention can provide the gas sensor element with high response characteristics capable of suppressing λ-point shift from being increased during the engine start and with high response characteristics during the stable operation of the internal combustion engine.

In the gas sensor element as another aspect of the present invention, the gas sensor element has a thickness ratio TA/TB within a range of not less than 1.5 and not more than 2.5 when the detection electrode is the full-surface electrode, and the thickness ratio TA/TB within a range of not less than 1.5 and not more than 2.0 when the detection electrode is the partial electrode, where TA is the thickness of the electrode protection layer in the bottom part and TB is the thickness of the electrode protection layer in the leg part.

When the gas sensor element has the full-surface electrode, having the thickness ratio $T_A/T_B$ within a range of not less than 1.5 and not more than 2.5 ($T_A/T_B$=1.5 to 2.5) makes it possible to decrease the λ-point shift and increase the response characteristics when compared with a gas sensor element with an electrode protection layer with a constant thickness.

Further, when the gas sensor element has the partial electrode, to have the thickness ratio $T_A/T_B$ within a range of not less than 1.5 and not more than 2.0 ($T_A/T_B$=1.5 to 2.0) makes it possible to decrease the λ-point shift and increase the response characteristics when compared with a gas sensor element with an electrode protection layer with a constant thickness.

In the gas sensor element as another aspect of the present invention, the gas sensor element has a supporting ratio $P_A/P_B$ within a range of not less than 1.6 and not more than 2.3 when the detection electrode is the full-surface electrode, and has the supporting ratio $P_A/P_B$ within a range of not less than 1.7 and not more than 2.0 when the detection electrode is the partial electrode, where $P_A$ is a catalyst supporting ratio of the electrode protection layer in the bottom part, and $P_B$ is a catalyst supporting ratio of the electrode protection layer in the leg part.

When the gas sensor element has the full-surface electrode, having the ratio (or supporting ratio) $P_A/P_B$ within a range of not less than 1.6 and not more than 2.3 ($P_A/P_B$=1.6 to 2.3) makes it possible to decrease the λ-point shift and increase the response characteristics when compared with a gas sensor element having an electrode protection layer with a constant thickness.

Further, when the gas sensor element has the partial electrode, having the supporting ratio $P_A/P_B$ within a range of not less than 1.7 and not more than 2.0 ($P_A/P_B$=1.7 to 2.0) makes it possible to decrease the λ-point shift and increase the response characteristics when compared with a gas sensor element having an electrode protection layer with a constant thickness.

In the gas sensor element as another aspect of the present invention, the electrode protection layer has a multi layer structure composed of at least two layers. A bottom layer as one layer in the multi layer structure of the electrode protection layer is directly in contact with the detection electrode, and made of metal oxide material composed of at least one of alumina, alumina magnesia spinel, and titanium. A catalyst layer as the other layer in the multi layer structure is formed on the outer surface of the bottom layer in the electrode protection layer, and the catalyst layer is made of metal oxide material and noble metal catalyst, where the metal oxide material is composed of at least one of alumina, alumina magnesia spinel, zirconia, and the noble metal catalyst is composed of at least one of platinum Pt, palladium Pd, rhodium Rh and ruthenium Ru.

According to the present invention, it is possible to optionally adjust the thickness and the catalyst supporting ratio of the catalyst layer in the electrode protection layer. This structure makes it possible to easily produce the gas sensor element in which the part having a high temperature rising speed has a large quantity of noble metal catalyst and the part having a low temperature rising speed has a low quantity of noble metal catalyst when the heater generated heat energy.

In accordance with another aspect of the present invention, there is provided a gas sensor which detects a concentration of a specific gas contained in a target detection gas. The gas sensor is comprised of the gas sensor element according to the present invention previously described, a housing case, an atmosphere cover case and an element cover case. In the housing case, the gas sensor element is placed. The atmosphere cover case is placed at a distal side of the housing case and covers the distal end part of the gas sensor element. The element cover case is placed at a front side of the gas sensor element and covers the front part of the gas sensor element.

According to the present invention, it is possible to provide the gas sensor equipped with the gas sensor element with a less λ-point shift during the beginning of the engine start and high response characteristics during the stable operation of the engine.

BRIEF DESCRIPTION OF THE DRAWINGS

A preferred, non-limiting embodiment of the present invention will be described by way of example with reference to the accompanying drawings, in which:

FIG. 3A is a view showing a cross section of the gas sensor element with a full-surface electrode according to a modification of the first embodiment of the present invention;

FIG. 3B is a view showing a cross section of the gas sensor element with a partial electrode according to a modification of the first embodiment of the present invention;

FIG. 3C is a view showing a temperature distribution on the surface of the gas sensor element according to the first embodiment of the present invention;

FIG. 9A is a view explaining various detection conditions regarding the test method of detecting the effects of the gas sensor element according to the present invention; and FIG. 9B is a view showing the method of evaluating the detection results of a step responsibility of the gas sensor element.

DETAILED DESCRIPTION OF THE PREFERRED EMBODIMENTS

Figure 1A:
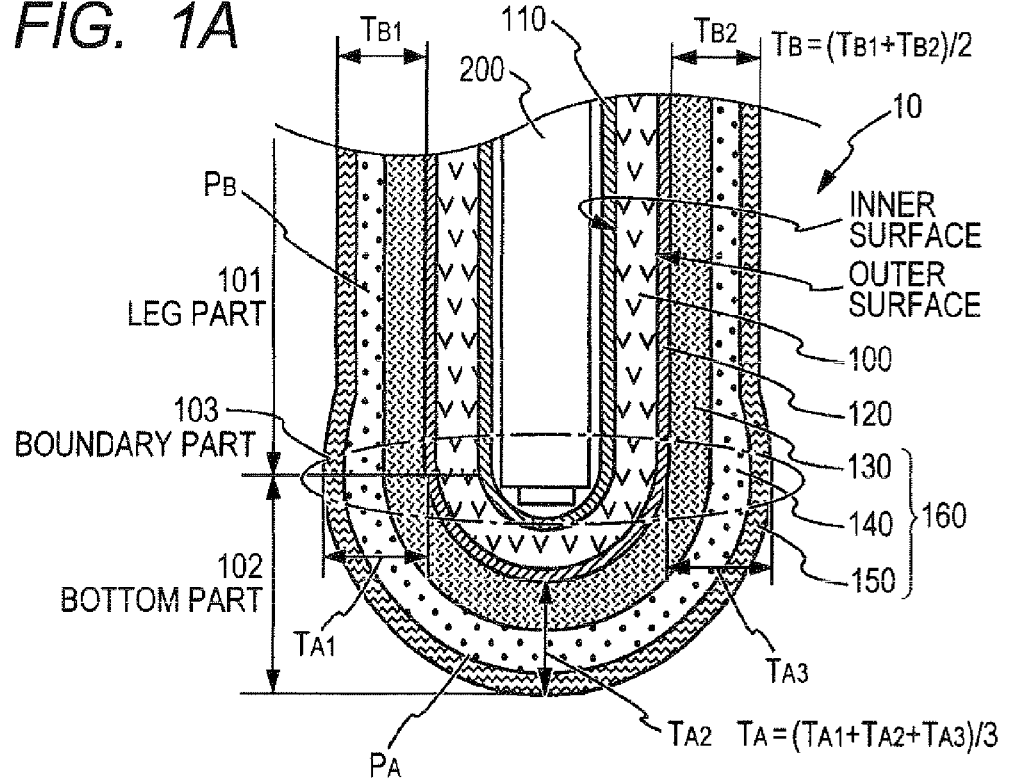
FIG. 1A is a view showing a cross section of a main part of a gas sensor element according to a first embodiment of the present invention.

Hereinafter, various embodiments of the present invention will be described with reference to the accompanying drawings. In the following description of the various embodiments, like reference characters or numerals designate like or equivalent component parts throughout the several diagrams.

First Embodiment

A description will be given of the gas sensor element 10 according to the first embodiment of the present invention with reference to FIG. 1A to FIG. 3C.

The gas sensor element and the gas sensor equipped with the gas sensor element according to the present invention can be applied to a feedback control of adjusting a combustion condition and a diagnosis of detecting fault of an exhaust gas purifying device of an internal combustion engine. That is, the gas sensor element and the gas sensor equipped with the gas sensor element according to the present invention are used to detect a concentration of a specific gas component such as oxygen and nitrogen oxide contained in target detection gas such as exhaust gas emitted from an internal combustion engine mounted to motor vehicles, and calculate an air/fuel ratio (A/F ratio) of the exhaust gas.

Figure 1B:
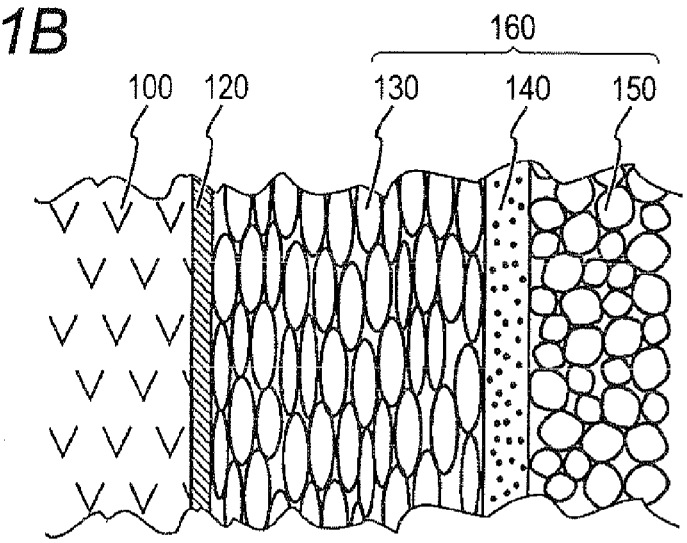
FIG. 1B is a view showing an enlarged cross section of the main part is of the gas sensor element shown in FIG. 1A.

FIG. 1A is a view showing a cross section of a main part of the gas sensor element 10 according to the first embodiment of the present invention. FIG. 1B is a view showing an enlarged cross section of the main part of the gas sensor element shown in FIG. 1A.

As shown in FIG. 1A, the gas sensor element 10 according to the first embodiment is comprised of a solid electrolyte body 100, a reference electrode 110, a detection electrode 120, a coating layer 130, a catalyst layer 140, and a poisoning layer 150. The coating layer 130, the catalyst layer 140 and the poisoning layer 150 form an electrode protection layer 160.

The solid electrolyte body 100 is made of solid electrolyte material such as zirconia (zirconium dioxide) having an oxygen ion conductivity. The solid electrolyte body 100 has a cylindrical shape with a bottom surface (or a closed base). A leg part 101 and a bottom part 102 are formed at the front side of the solid electrolyte body 100.

As shown in FIG. 1A, the profile of the leg part along an axial direction of the solid electrolyte body 100 has a line shape when a cross section of the solid electrolyte body 100 along an axial direction thereof is observed. On the other hand, the profile of the bottom part 102 along an axial direction of the solid electrolyte body 100 has a curved shape when a cross section of the solid electrolyte body 100 along an axial direction thereof is observed.

The reference electrode 110 and the detection electrode 120 are formed on the inner surface and the outer surface of the solid electrolyte body 100, respectively. The reference electrode 110 and the detection electrode 120 are made of conductive material such as platinum Pt.

In the configuration of the gas sensor element 10 according to the first embodiment, the detection electrode 120 is made of a full-surface electrode. That is, the entire of the leg part 101 and the bottom part 102 are covered with the full-surface electrode as the detection electrode 120.

The coating layer 130 is formed on the detection electrode 110 as an electrode protection layer capable of covering the detection electrode 120 and the outer surface of the solid electrolyte body 100. The coating layer 130 supports noble metal catalyst. Through the coating layer 130, a target detection gas passes. Further, the coating layer 130 covers the surface of the detection electrode 110 and is made of metal oxide material mainly composed of at least one of alumina, magnesia spinel and titanium.

The catalyst layer 140 is formed in the gas sensor element 10 so that the catalyst layer 140 covers the outer surface of the coating layer 130 and is made of metal oxide material and noble metal catalyst. The metal oxide material is made of at least one of alumina, alumina magnesia spinel and zirconia (zirconium dioxide). The noble metal catalyst is made of at least one of platinum Pt, palladium Pd, rhodium Rh and ruthenium Ru.

The poisoning layer 150 is formed on the catalyst layer 140 in the gas sensor element 10 so as to cover the outer surface of the catalyst layer 140. The poisoning layer 150 is made of metal oxide material composed of at least one of alumina, alumina magnesia spinel and titanium.

The heater 200 is inserted and placed in the inside of the solid electrolyte body 100. When receiving electric power, the heater 200 generates heat energy.

The electrode protection layer 160 is comprised of the coating layer 130, the catalyst layer 140 and the poisoning layer 150.

As shown in FIG. 1A, the electrode protection layer 160 has the thicknesses $T_{A1}$ and $T_{A3}$ at the boundary part between the leg part 101 and the bottom part 102 in the gas sensor element 10. The electrode protection layer 160 at the bottom part 102 in the gas sensor element 10 has the thicknesses $T_{A2}$. The electrode protection layer 160 has the thicknesses $T_{B1}$ and $T_{B2}$ at the leg part 101 in the gas sensor element 10.

The gas sensor element 101 according to the first embodiment has the following relationship.

Each of $T_{A1}$, $T_{A3}$ and/or $T_A$ ($=(T_{A1}+T_{A2}+T_{A3})/3$) is larger than $T_B$ ($=(T_{B1}+T_{B2})/2$).

Specifically, the electrode protection layer 160 composed of the coating layer 130, the catalyst layer 140 and the poisoning layer 150 has a thickness ratio $T_A/T_B$ within a range of not less than 1.5 to not more than 2.5, where $T_A$ is the thickness of the electrode protection layer 160 at the bottom part 102, $T_B$ is the thickness of the electrode protection layer 160 at the leg part 101, and $T_A/T_B$ indicates a ratio of thickness of the electrode protection layer 160 between the bottom part 102 and the leg part 101.

When the heater 200 which is placed in the inside of the solid electrolyte body 100 receives electric power and generates heat energy, the gas sensor element 10 is heated. The bottom part 102 and/or the boundary part 103 between the bottom part 102 and the leg part 101 have a high temperature rising speed.

A description will be given of a method of producing the gas sensor element according to the first embodiment of the present invention.

The solid electrolyte body 100 is made of zirconia powder. The zirconia powder is produced by firing a predetermined quantity of yttria by using a known method such as extruding mold method, press mold method, cold isostatic pressing (CIP) method, and hot isostatic pressing (HIP) method.

After forming a cylindrical shape having a base part (or a closed base) in which one end part of the cylindrical shape is opened and the other end part is closed, the solid electrolyte body 100 is fired at a temperature within a range of 1400° C. to 1600° C.

The reference electrode 110 and the detection electrode 120 are made of platinum Pt and formed by using a known method such as vacuum evaporation and chemical plating.

Next, the coating layer 130 as the bottom layer of the electrode protection layer 160 is formed on the surface of the detection electrode 120 so that the coating layer 130 is directly in contact with the detection electrode 120 by applying a slurry or paste of the metal oxide material on the detection electrode 120 and adhering a green sheet on the detection electrode 120 by using firing, plasma powder spraying. The slurry or paste is made of metal oxide material composed of at least one of alumina, alumina zirconia spinel, and titanium.

Further, slurry is made by using metal oxide material composed of at least one of alumina, alumina magnesia spinel, zirconia and noble metal catalyst composed of at least one of platinum Pt, palladium Pd, rhodium Rh and ruthenium Ru. The catalyst layer 140 is formed by immersing the solid electrolyte body 100 on which the coating layer 130 is formed is immersed into the slurry. The solid electrolyte body 100 is dried and fired so as to produce the catalyst layer 140 on the coating layer 130 of the solid electrolyte body 100.

In the above producing period of time, it is possible to adjust the thickness of the catalyst layer 140 by adjusting (increasing or decreasing) the number of the steps to immerse the solid electrolyte body 100 into the slurry or by adjusting the pulling speed of the solid electrolyte body 100 from the slurry. This makes it possible to adjust the total quantity of noble metal catalyst contained in the catalyst layer 140 at the boundary part 103 between the leg part 101 and the bottom part 102, and/or the bottom part 102. For example, it possible to increase the total quantity of noble metal catalyst contained in the catalyst layer 140 and/or the bottom part 102 compared to the total quantity of the noble metal catalyst contained in the catalyst layer 140 in the leg part 101.

When the catalyst layer 140 is formed on the coating layer 130, it is possible to deposit and grow noble metal catalyst on the grain surface of thermal resistance metal oxide material after the solid electrolyte body 100 is immersed in a solution composed of the thermal resistance metal oxide particles such as alumina and catalyst metal salt, dried, and thermal-processed.

After forming the catalyst layer 140 on the coating layer 130, slurry is made by using metal oxide material composed of at least one of alumina, alumina magnesia spinel and zirconia. The solid electrolyte body 100 with the catalyst layer 140 is immersed into this slurry, dried, and fired in order to produce the poisoning layer 150. Thus, the gas sensor element 10 is produced by the above method.

Further, it is possible to use inorganic binder such as alumina sol and silica sol so as to produce the poisoning layer 150.

In the gas sensor element 100 according to the first embodiment of the present invention, the catalyst layer 140 in the bottom part 102 and the catalyst layer 140 in the leg part 101 have a different quantity of catalyst in order to have the feature in which the catalyst layer 140 in the bottom part 102 and catalyst layer 140 in the leg part 101 have the supporting rates $P_A$ and $P_B$ of supporting the noble catalyst, respectively, and the supporting rate $P_A$ and the supporting rate $P_B$ are the same value.

Still further, the electrode protection layer 160 is comprised of the coating layer 130, the catalyst layer 140 and the poisoning layer 150 in the gas sensor element 100 according to the first embodiment. The present invention is not limited by this structure. It is possible to form the electrode protection layer 160 by using a coating layer 130a and the poisoning layer 150. For example, as shown in FIG. 5B, the coating layer 130a contains noble metal catalyst 140a. That is, the coating layer 130a is directly supports the noble metal catalyst 140a. The structure of the coating layer 130a will be explained later in detail.

A description will now be given of the gas sensor 1 equipped with the gas sensor element 10 having the above structure with reference to FIG. 2.

Figure 2:
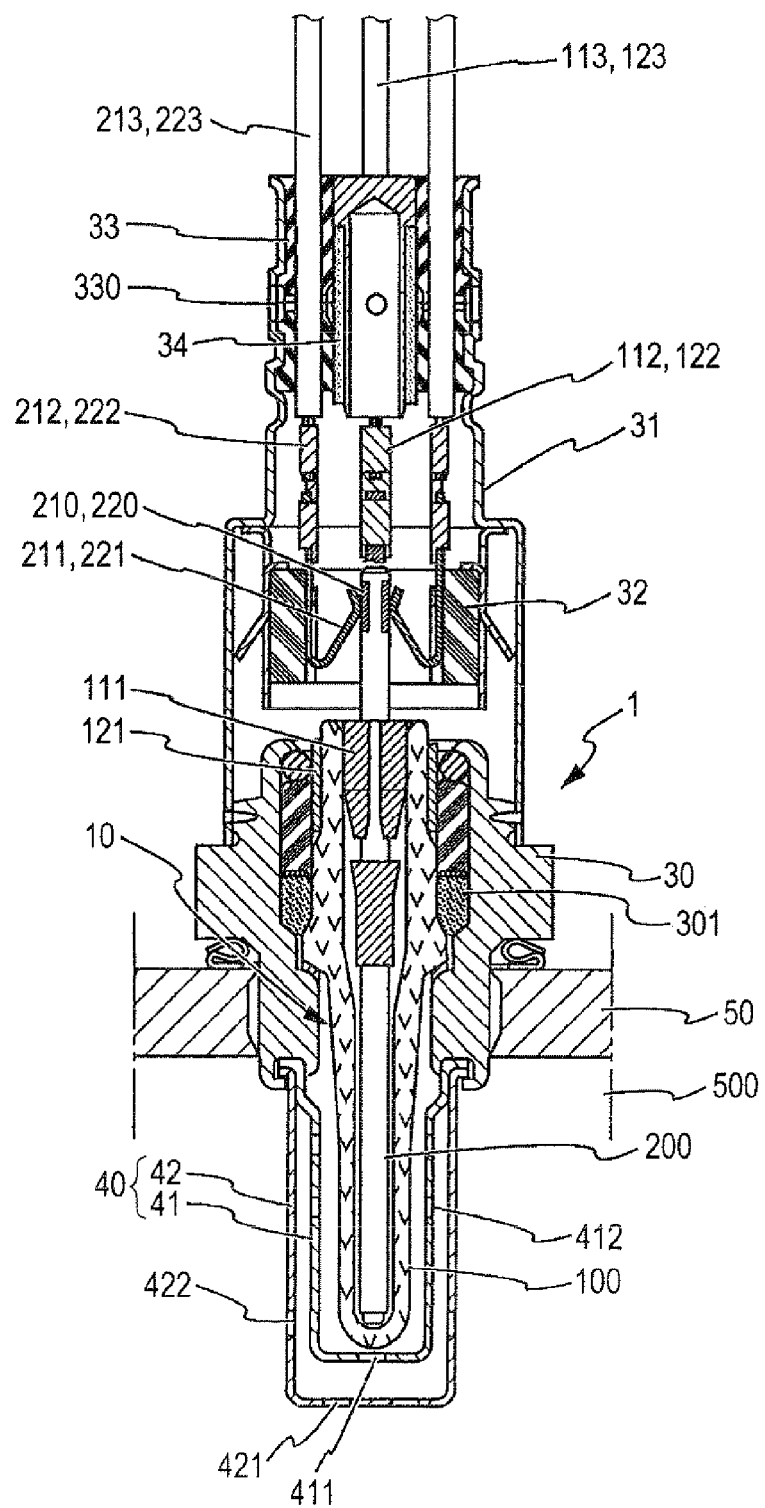
FIG. 2 is a view showing a cross section of a gas sensor equipped with the gas sensor element according to the first embodiment of the present invention shown in FIG. 1A and FIG. 1B.

FIG. 2 is a view showing a cross section of the gas sensor 1 equipped with the gas sensor element 10 according to the first embodiment of the present invention shown in FIG. 1A and FIG. 1B.

As shown in FIG. 2, the gas sensor 1 is comprised of a housing case 30, an atmosphere cover 31 and an element cover 40. The heater 20 is inserted, placed in and fixed to the inside of the gas sensor element 10. The gas sensor element 10 is inserted and placed in the inside of the housing case 30. The atmosphere cover 31 is placed at the distal end of the housing case 30. The distal end of the gas sensor element 10 is covered with the atmosphere cover 31. The element cover 40 is placed at the front end of the housing case 30. The front end of the gas sensor element 10 is covered with the element cover 40.

The housing case 30 is fixed to the wall surface of a target detection gas passage 50 through which the target detection gas 500 flows. The front part of the gas sensor element 10 is placed in the flow of the target detection gas in the target detection gas passage 50. The gas sensor element 10 is fixed with a sealing member 301 to the inside of the housing case 30 made of metal having a cylindrical shape. The atmosphere cover 31 is fixed to the opening part at the distal end of the housing case 30. The element cover 40 is fixed to the opening part at the distal end of the housing case 30.

As shown in FIG. 2, the element cover 40 has a double cylindrical structure composed of an inner cover 41 and an outer cover 42. Opening parts (or inlet parts) 411, 412, 421 and 422 are formed in the side surface and the bottom surface of each of the inner cover 41 and the outer cover 42.

The double cylindrical structure of the element cover 40 prevents water from entering the inside of the gas sensor element 10, and promotes entering the target detection gas 500 into the front side of the gas sensor element 10.

The heater 200 is elastically supported in the inside of the gas sensor element 10 by using a heater supporting metal fitting 111 having a cylindrical shape. When receiving electric power, the heater 200 generated heat energy.

The heater supporting metal fitting 111 acts as the reference electrode 110 placed in the inside of the solid electrolyte body 100 and a reference electrode terminal which is electrically connected to the reference electrode 110. The heater supporting metal fitting 111 is electrically connected to a detection device (not shown) placed in the outside of the gas sensor 1 through the terminal metal fitting 112 and a signal line 113.

A detection electrode terminal 121 having a ring shape is fitted to the outer periphery of the gas sensor element 10. The detection electrode terminal 121 is electrically connected to the detection device (not shown) through a terminal metal fitting 122 and a signal line 123.

Conductive terminals 210 and 220 are formed at the distal end of the heater 200. The conductive terminals 210 and 220 are electrically connected to terminal metal fittings 211 and 221. The conductive terminals 210 and 220 are further electrically connected to a power supply control device through connection metal fittings 212, 222, conductive lines 213 and 223.

An insulator 32 is elastically supported in the inside of the atmosphere cover 31. The insulator 32 fixes and insulates the terminal metal fittings 112, 122, 212 and 222 from each other.

The distal end part of the atmosphere cover 31 fixes the signal lines 113, 123, and the conductive lines 213 and 223 through elastic member 33. These signal lines and the conductive lines 213 and 223 are sealed in the atmosphere cover 31.

An atmosphere introduction hole 330 is formed in the atmosphere cover 31 and the elastic member 33. Atmosphere gas is introduced into the surface of the reference electrode 110 formed in the inside of the gas sensor 10 through a water repellency filter 34 and the atmosphere introduce hole 330.

For example, when the gas sensor 1 equipped with the gas sensor element 10 according to the first embodiment is used as an oxygen sensor, an oxygen concentration cell is formed by a difference between the concentration of oxygen contained in the atmosphere gas in contact with the surface of the reference electrode and the concentration of oxygen contained in the target detection gas in contact with the surface of the detection electrode 120. The outside detection means detects the electromotive power generated between the reference electrode 110 and the detection electrode 120. The outside detection means can detect the concentration of oxygen contained in the target detection gas and the concentration of nitrogen oxide contained in the target detection gas on the basis of the detected electromotive force.

In the gas sensor 1 according to the first embodiment, the quantity of noble metal catalyst contained in the electrode protection layer 160 (which is composed of the coating layer 130, the catalyst layer 140 and the poisoning layer 150) in the bottom part 102 is larger than the quantity of noble metal catalyst contained in the electrode protection layer 160 in the leg part 102. When the heater 200 generates heat energy and the generated heat energy is supplied to the electrode protection layer 160, the bottom part 102 in the electrode protection layer 160 gas a high temperature rising speed, and the leg part 101 in the electrode protection layer 160 has a low temperature rising speed. Accordingly, at the beginning of the engine start, the noble metal catalyst contained in the electrode protection layer 160 in the bottom part 102 purifies hydrogen contained in the target detection gas. This can suppress a λ-point from being shifted. On the other hand, when the entire of the gas sensor 1 is adequately heated and the gas sensor 1 becomes its stable temperature condition, the quantity of the target detection gas adsorbed to the noble metal catalyst in the electrode protection layer 160 becomes low and a diffusion speed is not decreased because the electrode protection layer 160 in the leg part 101 has a less quantity of the noble metal catalyst. This makes it possible for the gas sensor 1 equipped with the gas sensor element 10 according to the first embodiment to maintain a high response characteristics.

In the structure of the gas sensor element 10 according to the first embodiment, it is possible to form the catalyst layer 140 with a desired and optional thickness. When the gas sensor element 1 has the structure in which the thickness $T_A$ of the bottom part 102 is larger than the thickness $T_B$ of the leg part 101, it is possible to increase the quantity of noble metal catalyst in the electrode protection layer 160 in the first part and decrease that in the second part, where the first part (as the bottom part 102) has a high temperature rising speed and the second part (as the leg part 101) has a low temperature rising speed when the heater 200 generates heat energy and the gas sensor element 10 is activated by the generated heat energy.

FIG. 3A is view showing a cross section of the solid electrolyte body 100 in the gas sensor element with the full-surface electrode 120 according to a modification of the first embodiment of the present invention. FIG. 3B is a view showing a cross section of the solid electrolyte body 100P in the gas sensor element with the partial-surface electrode 120P according to a modification of the first embodiment of the present invention. FIG. 3C is a view showing a temperature distribution on the surface of the gas sensor element according to the first embodiment of the present invention.

It is possible for the detection electrode formed on the outer surface of the solid electrolyte body 100 to have the structure of the full-surface electrode 120 which is formed on the entire surface of the bottom part 101 and the leg part 102 shown in FIG. 3A. Further, it is possible for the detection electrode formed on the outer surface of the solid electrolyte body 100P to have the structure of the partial electrode 120P which is formed on the surface of the leg part 101 only.

In both the structures shown in FIG. 3A and FIG. 3B, the front part of the solid electrolyte body 100, 100P has a high temperature, and the temperature is gradually decreased to the distal end part thereof.

In particular, at the beginning of the engine start, temperature of the surface of the solid electrolyte body 100 at the bottom part 102 becomes approximately a temperature of not less than 400° C., the solid electrolyte body 100 shows oxygen ion conductivity, and the noble metal catalyst contained in the catalyst layer 140 is also activated. On the other hand, because the solid electrolyte body 100 at the leg part 101 of the gas sensor element 10 has a low temperature when compared with the temperature of the bottom part 102, the solid electrolyte body 100 at the leg part 101 does not show the oxygen ion conductivity. Accordingly, the solid electrolyte body 100 at the leg part 101 does not detect a concentration of oxygen ion contained in the target detection gas.

Second Embodiment

A description will be given of the gas sensor element 10a according to a second embodiment of the present invention with reference to FIG. 4, FIG. 5A, FIG. 5B and FIG. 5C.

Figure 4:
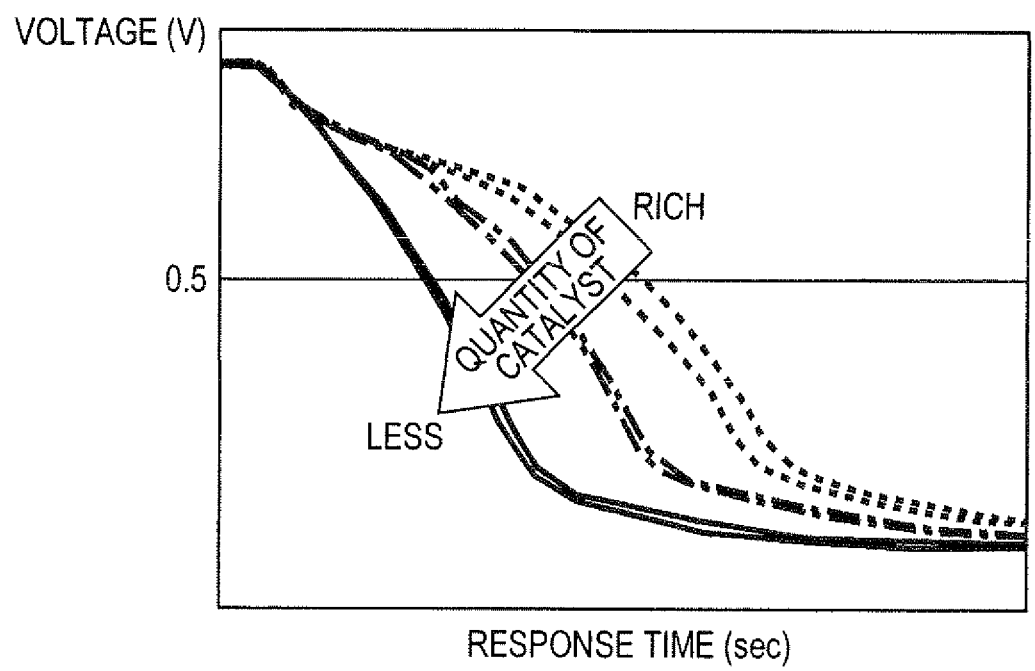
FIG. 4 is a view showing a response characteristic of a conventional gas sensor element having a conventional structure when a catalyst quantity is changed.

At first, the second embodiment explains the relationship between the quantity of catalyst contained in an electrode protection layer and a response characteristic of a conventional gas sensor with reference to FIG. 4.

FIG. 4 is a view showing a response characteristic of a conventional gas sensor element having a conventional structure when the quantity of catalyst is changed.

That is, FIG. 4 shows the response characteristics of gas sensors having a different quantity of catalyst supported on a catalyst layer when the value λ is continuously changed within a range of 0.9995 to 1.0005 and a target detection gas contain hydrogen of a constant concentration and oxygen having a different concentration.

As shown in FIG. 4, when the quantity of catalyst (or catalyst particles) supported on the catalyst layer is increased, the response time of the gas sensor is delayed. This means that catalyst particles adsorb oxygen contained in the target detection gas, and the diffusion speed of the target detection gas is thereby decreased. The more the quantity of catalyst grains supported on the catalyst layer is decreased, the more the response characteristic of the gas sensor is increased. However, when the target detection gas contains hydrogen rich, for example, at the beginning of the engine start, the catalyst in the gas sensor cannot adequately purify oxygen, and this often causes such a λ-point shift.

The gas sensor according to the second embodiment of the present invention can solve the above conventional problem.

Figure 5A:
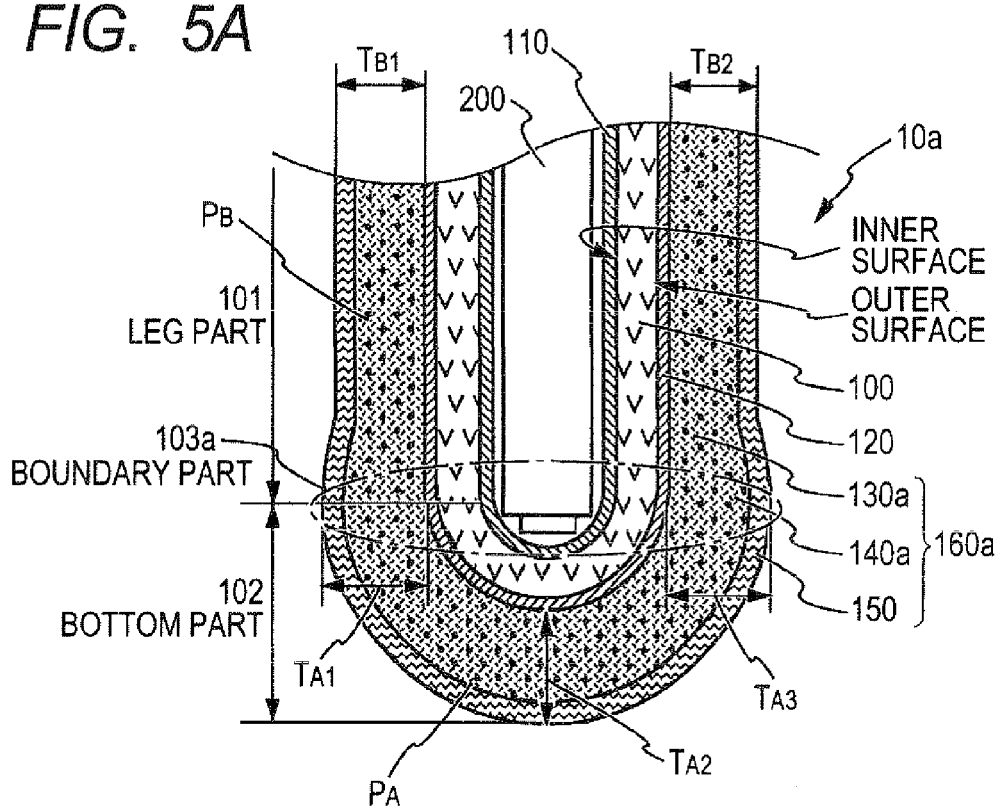
FIG. 5A is a view showing a cross section of a main part of a gas sensor element according to a second embodiment of the present invention.
Figure 5B:
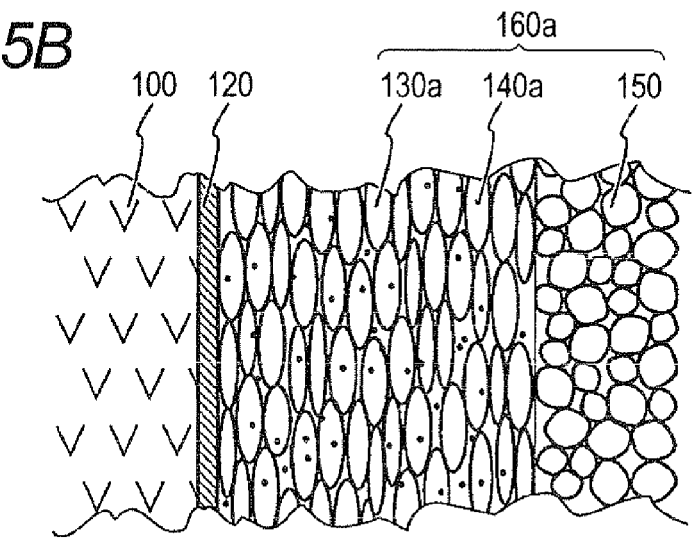
FIG. 5B is a view showing an enlarged cross section of the main part of the gas sensor element shown in FIG. 5A.

FIG. 5A is a view showing a cross section of a main part of the gas sensor element 10a according to the second embodiment of the present invention. FIG. 5B is a view showing an enlarged cross section of the main part of the gas sensor element 10a shown in FIG. 5A.

The same components between the first and second embodiments will be referred with the same reference numbers.

By the way, as previously described, the first embodiment shows the method of producing the gas sensor element 10 having the structure in which the catalyst layer 140 shown in FIG. 1A and FIG. 1B is formed on the outer surface of the coating layer 130 after the coating layer 130 is formed.

On the other hand, in the method according to the second embodiment shown in FIG. 5A and FIG. 5B, noble metal catalyst 140a in the gas sensor element 10a is directly supported on the coating layer 130a.

Specifically, after forming the coating layer 130a by a known method such as plasma spraying using alumina, the solid electrolyte body with the coating layer 130a is immersed into a solution composed of catalyst metal sold solution such as $H_2PtCl_6$. After this, under a low pressure condition, the catalyst metal sold is entered into the coating layer 130a. The solid electrolyte body with the coating layer 130a containing noble metal catalyst 140a is dried and fired. It is also possible to produce and grow noble metal catalyst 140a on the surface of the anti-thermal metal oxide material in order to produce the coating layer 130a with noble metal catalyst 140a.

The gas sensor element 10a having the above structure and produced by the above method can have the same effects of the first embodiment. That is, when the bottom thickness of the electrode protection layer 160a is thicker than the leg thickness of the electrode protection layer 160a, it is possible to form the noble metal catalyst in the electrode protection layer 160a (composed of the coating layer 130a with noble metal catalyst 140a and the poisoning layer 150a) in the bottom part 102 which is greater in quantity of noble metal catalyst than that in the leg part 101. The bottom part 102 is rapidly heated and activated more than the leg part 101 by the heater 200.

Third Embodiment

A description will be given of the gas sensor element 10b according to the third embodiment of the present invention with reference to FIG. 6A and FIG. 6B.

Figure 6A:
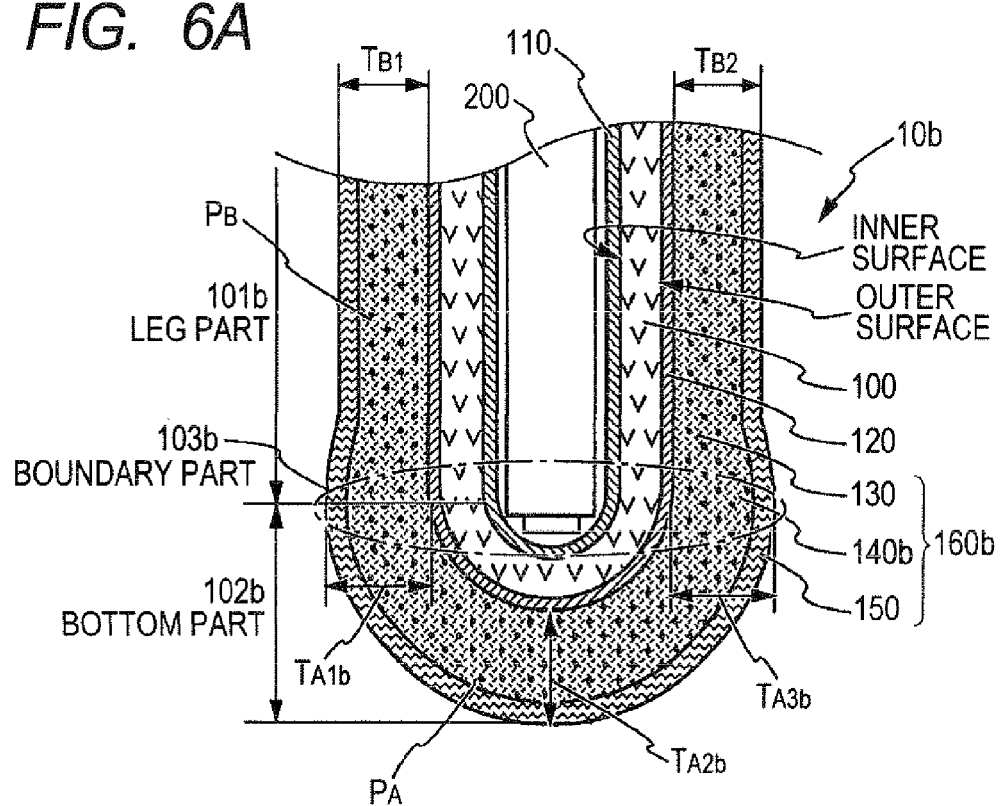
FIG. 6A is a view showing a cross section of a main part of a gas sensor element according to a third embodiment of the present invention.
Figure 6B:
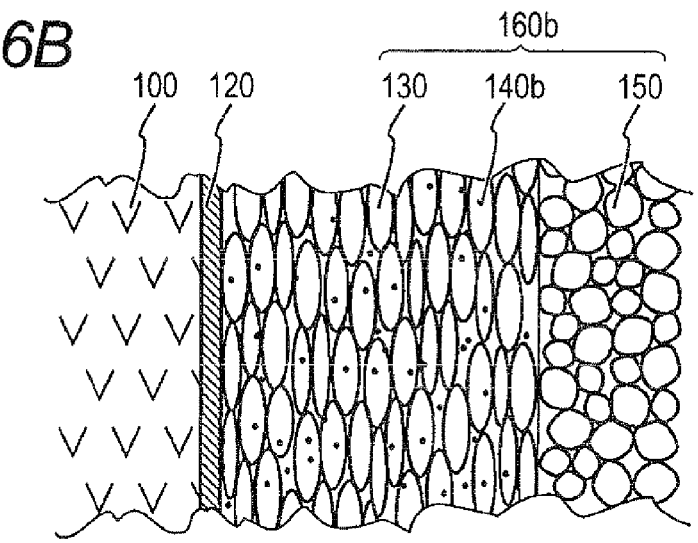
FIG. 6B is a view showing an enlarged cross section of the main part of the gas sensor element shown in FIG. 6A.

FIG. 6A is a view showing a cross section of a main part of the gas sensor element 10b according to the third embodiment of the present invention. FIG. 6B is a view showing an enlarged cross section of the main part of the gas sensor element 10b shown in FIG. 6A.

The first and second embodiments previously described adjust the quantity of noble metal catalyst by changing the thickness of the electrode protection layer 160, 160a. That is, the leg part 101 and the bottom part 102 in the gas sensor element according to the first and second embodiments have the same catalyst supporting ratio, but a different thickness.

On the other hand, the third embodiment adjusts the quantity of noble metal catalyst by changing the catalyst supporting ratio in the leg part 101b and the bottom part 102b of the gas sensor element 10b.

Specifically, the electrode protection layer 160b (composed of the coating layer 130, the catalyst layer 140b, and the poisoning layer 150) in the bottom part 102b and the boundary part 103b between the leg part 101b and the bottom part 102b has the catalyst supporting ratio $P_A$ which is higher than the catalyst supporting ratio $P_B$ in the leg part 101b.

In more detail, when the catalyst supporting ratio in the bottom part 102b is $P_A$ and the catalyst supporting ratio in the leg part 101b is $P_B$, the gas sensor element 10b according to the third embodiment has the supporting ratio $P_A/P_B$ within a range of not less than 1.6 and not more than 2.3 because the detection electrode 120 has the full-surface electrode.

The supporting ratio $P_A/P_B$ of the catalyst supporting ratios $P_A$ and $P_B$ can be detected by cutting the gas sensor element and observing the cut surface of the gas sensor element by using a scanning electron microscope (SEM).

Specifically, each area 10 μm$^2$ in back scattered electron image (BEI) of several ten thousand times is observed. White-color particles having a circle shape as noble metal catalyst in the observation result are calculated. The calculated result is converted in weight to obtain a weight per area. The obtained value of weight per area is used as the catalyst supporting ratio.

The catalyst supporting ratio $P_A$ of the bottom part 102b is obtained on the basis of the average catalyst supporting ratio by detecting the thickness $T_{A3b}$ at four points in the boundary part 103b and the thickness $T_{A2b}$ at two points in the bottom part 102b.

The catalyst supporting ratio $P_B$ of the leg part 101b is obtained on the basis of the average catalyst supporting ratio by detecting the thickness $T_{A1b}$ at four points in the leg part 101b which is separated from the boundary part 103b by 5 mm.

In order for the leg part 101b and the bottom part 102b to have a different catalyst supporting ratio and change the catalyst supporting ratio, it is possible to form the catalyst layer 140b by applying a slurry having a rich quantity of noble metal catalyst on the bottom part 102b and drying and firing it, and then applying a slurry having noble metal catalyst of a less quantity on the coating layer 130, and drying and firing it.

Instead of the above method, when noble metal catalyst is directly supported on the coating layer 103b, it is possible to immerse the coating layer 103b with the leg part 101b and the bottom part 102b in catalyst metal salt solution, and to immerse the coating layer 103b with the bottom part 102b only plural times. This method makes it possible to increase the quantity of noble metal catalyst supported in the bottom part 102b.

Fourth Embodiment

A description will be given of the gas sensor element 10c according to the fourth embodiment of the present invention with reference to FIG. 7A and FIG. 7B.

Figure 7A:
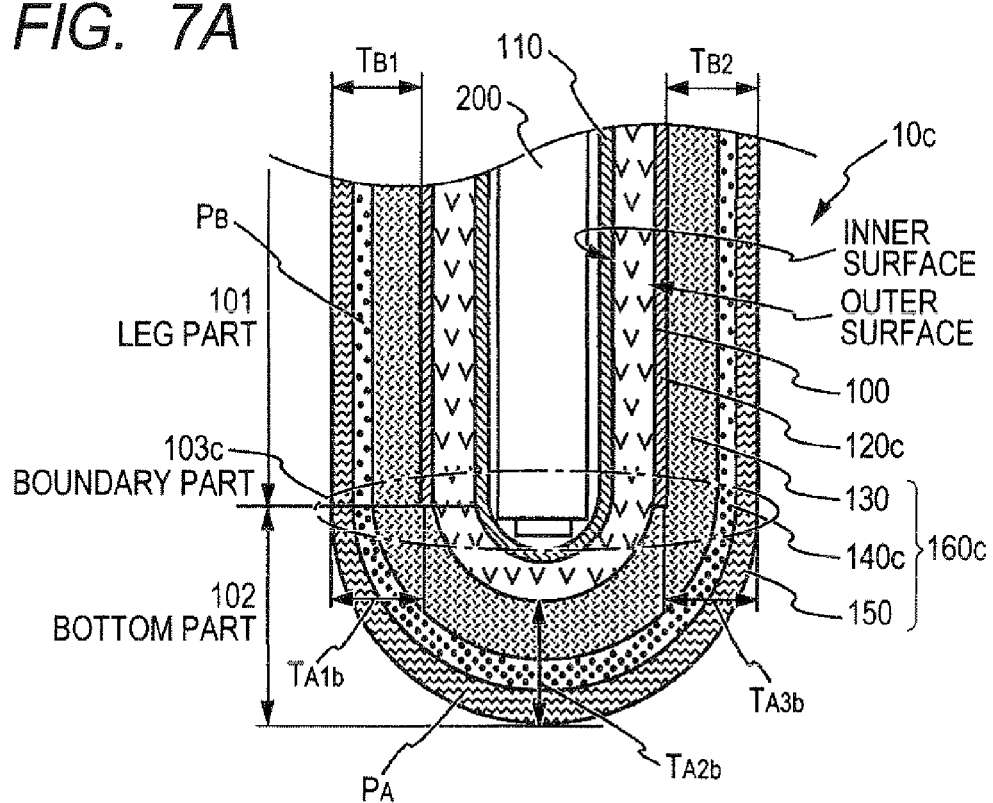
FIG. 7A is a view showing a cross section of a main part of a gas sensor element according to a fourth embodiment of the present invention.
Figure 7B:
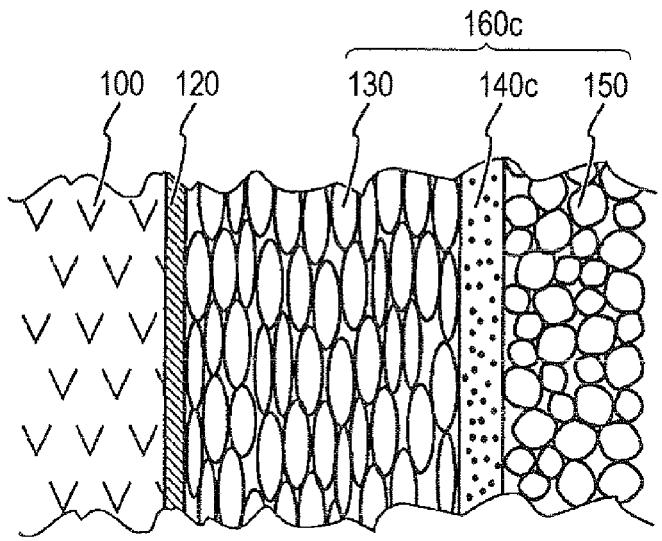
FIG. 7B is a view showing an enlarged cross section of the main part of the gas sensor element shown in FIG. 7A.

FIG. 7A is a view showing a cross section of a main part of the gas sensor element 10c according to the fourth embodiment of the present invention. FIG. 7B is a view showing an enlarged cross section of the main part of the gas sensor element 10c shown in FIG. 7A.

In the first, second and third embodiments disclose the gas sensor element having the full-surface detection electrode 120. On the other hand, the fourth embodiment will show the gas sensor element 10c having a partial detection electrode 120c.

In particular, the gas sensor element 10c according to the fourth embodiment has a thickness ratio $T_A/T_B$ within a range of not less than 1.5 and not more than 2.0.

Further, it is also possible for the gas sensor element 10c according to the fourth embodiment to have the thickness ratio $T_A/T_B$ within a range of not less than 1.7 and not more than 2.0.

Still further, it is also possible for the gas sensor element 10c according to the fourth embodiment to have the thickness ratio $T_A/T_B$ within a range of not less than 1.5 and not more than 2.0, and to have the noble catalyst supporting ratio $P_A/P_B$ within a range of not less than 1.7 and not more than 2.0.

A description will now be given of the experimental test in order to verify and confirm the effects of the gas sensor element according to the present invention with reference to FIG. 8A, FIG. 8B, FIG. 9A and FIG. 9B.

Figure 8A:
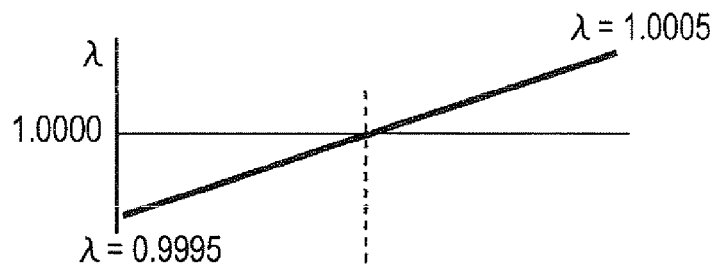
FIG. 8A is a view showing a test method of detecting the effects of the gas sensor element according to the present invention capable of solving a λ-shift problem.
Figure 8B:
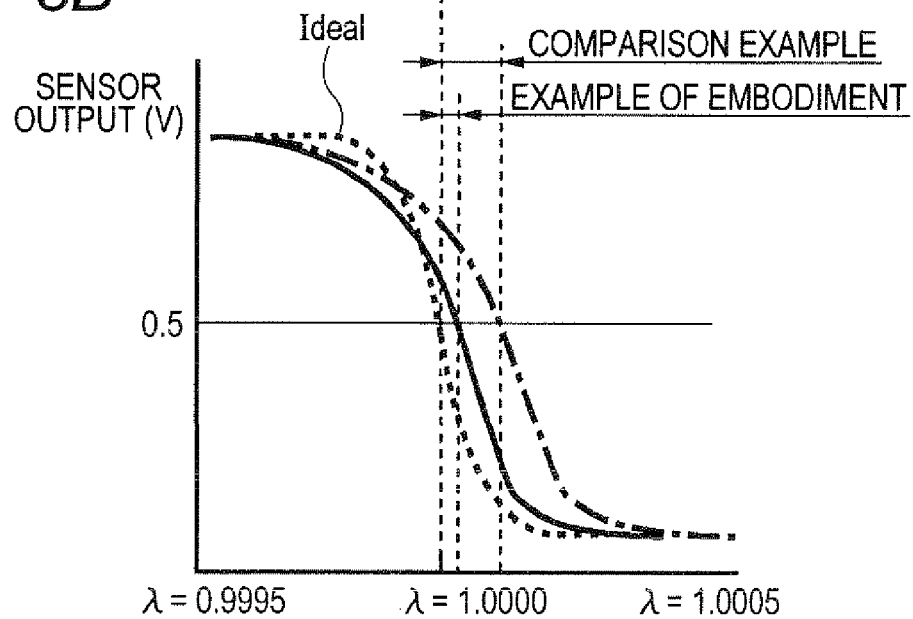
FIG. 8B is a view showing the effects of the gas sensor element according to the present invention capable of solving the λ-shift problem and also showing a comparison example.

FIG. 8A is a view showing a test method of detecting the effects of the gas sensor element according to the present invention capable of solving a λ-shift problem. FIG. 8B is a view showing the effects of the gas sensor element according to the present invention capable of solving the λ-shift problem and also showing a comparison example.

As shown in FIG. 8A, the fourth embodiment detected the output and λ-point shift of the gas sensor element by using various target detection gas having a constant concentration of hydrogen and a different concentration of oxygen while λ-point is changed from 0.9995 to 1.0005 and the thickness of the electrode protection layer is changed, as shown in FIG. 8B.

FIG. 9A is a view explaining various detection conditions regarding the test method of detecting the effects of the gas sensor element according to the present invention. FIG. 9B is a view showing the method of evaluating the detection results of a step responsibility of the gas sensor element.

As shown in FIG. 9A, the fourth embodiment detected an average value of a rich to lean switching response period $T_{RL}$ and a lean to rich switching response period $T_{LR}$ when the output of the gas sensor element indicates a response of 63% while rich gas and lean gas are alternately switched as the target detection gas. The rich gas is a mixture of CO, $CH_4$ and $C_3H_8$ having 0.9995 of the air/fuel (A/F) ratio, and the lean gas is a mixture of $O_2$ and NO so as to obtain 1.0005 of the A/F ratio. The fourth embodiment detected the step response characteristic of the gas sensor element while the thickness of the electrode protection layer of the gas sensor element is changed.

Table 1 and Table 2 show the experimental results of the fourth embodiment. In particular, Table 1 shows the experimental results of the gas sensor element with the full-surface electrode, and Table 2 shows the experimental results of the gas sensor element with the partial electrode.

In Table 1 and Table 2, because sample No. 2 as a reference sample had the λ-point shift of 0.0009, when the output voltage of these samples had 0.5 V, in which the leg part 101 and the bottom part 102 had the same thickness $T_A=T_B=20$ μm, the fourth embodiment judged that a sample having the λ-point shift of more than 1.0001 had no effect and designated the sample with the reference symbol "Δ", a sample having the λ-point shift of not more than 1.001 and more than 1.0005 had the effect and designated the sample with the reference symbol "O", and a sample having the λ-point shift of not more than 1.005 had a superior effect and designated the sample with the reference symbol "Φ".

In addition, because reference sample No. 9 as a reference sample had the step response time of 15 seconds, in which the leg part 101 and the bottom part 102 had the same thickness $T_A = T_B = 20$ μm, the fourth embodiment judged that a sample having the step response time of more than 15 seconds had no effect and designated the sample with the reference symbol "Δ", a sample having the λ step response time of not more than 15 seconds had the effect and designated the sample with the reference symbol "O".

protection layer 160 (composed of the coating layer 130, the catalyst layer 140 and the poisoning layer 150) is changed. Table 3 and Table 4 show the experimental results. In particular, Table 3 shows the experimental results of the gas sensor element with the full-surface electrode, and Table 4 shows the experimental results of the gas sensor element with the partial electrode.

In Table 3, because sample No. 15 as a reference sample had the λ-point shift of 0.0009, when the output voltage of these sample had 0.5 V, in which the leg part 101 and the bottom part 102 had the same catalyst supporting ratio $P_A = P_B = 35$ μg/mm², the fourth embodiment judged that a sample having the λ-point shift of more than 1.0001 had no effect and designated the sample with the reference symbol "Δ", a sample having the λ-point shift of not more than 1.001

TABLE 1

| Sample No. | Thickness (μm) Bottom part TA | Thickness (μm) Leg part TB | Thickness ratio TA/TB | λ-point shift Amount | λ-point shift Result | 63% response characteristic Response time | 63% response characteristic Result |
|---|---|---|---|---|---|---|---|
| 1 | 17 | 20 | 0.9 | 0.0011 | Δ | 13 seconds | ○ |
| 2 | 20 | 20 | 1.0 | 0.0009 | — | 15 seconds | — |
| 3 | 22 | 20 | 1.1 | 0.0008 | ○ | 15 seconds | ○ |
| 4 | 30 | 20 | 1.5 | 0.0005 | Φ | 15 seconds | ○ |
| 5 | 40 | 20 | 2.0 | 0.0004 | Φ | 15 seconds | ○ |
| 6 | 50 | 20 | 2.5 | 0.0004 | Φ | 15 seconds | ○ |
| 7 | 53 | 20 | 2.7 | 0.0004 | Φ | 17 seconds | Δ | and more than 1.0005 had the effect and designated the

TABLE 2

| Sample No. | Thickness (μm) Bottom TA | Thickness (μm) Leg TB | Thickness ratio TA/TB | λ-point shift Amount | λ-point shift Result | 63% response characteristic Response time | 63% response characteristic Result |
|---|---|---|---|---|---|---|---|
| 8 | 17 | 20 | 0.9 | 0.0011 | Δ | 13 seconds | ○ |
| 9 | 20 | 20 | 1.0 | 0.0009 | — | 15 seconds | — |
| 10 | 22 | 20 | 1.1 | 0.0008 | ○ | 15 seconds | ○ |
| 11 | 30 | 20 | 1.5 | 0.0005 | Φ | 15 seconds | ○ |
| 12 | 40 | 20 | 2.0 | 0.0004 | Φ | 15 seconds | ○ |
| 13 | 45 | 20 | 2.3 | 0.0004 | Φ | 16 seconds | Δ |

As can be understood from the experimental results show in Table 1 and Table 2, it is preferable for the thickness ratio $T_A/T_B$ to have a range of not less than 1.5 and not more than 2.5 when the detection electrode in the gas sensor element has the full-surface electrode, and it is preferable for the thickness ratio $T_A/T_B$ to have a range of not less than 1.5 and not more than 2.0 when the detection electrode in the gas sensor element has the partial electrode, where the electrode protection layer 160 (which is composed of the coating layer 130, the catalyst layer 140 and the poisoning layer 150) has the thickness $T_A$ in the bottom part 102 and the thickness $T_B$ in the leg part 101.

The same experiment previously described was executed while the catalyst supporting ratio contained in the electrode sample with the reference symbol "O", and a sample having the λ-point shift of not more than 1.0005 had a superior effect and designated the sample with the reference symbol "Φ".

In addition, In Table 4, because sample No. 22 as a reference sample had the step response time of 15 seconds, in which the leg part 101 and the bottom part 102 had the same catalyst supporting ratio $P_A = P_B = 35$ μg/mm², the fourth embodiment judged that a sample having the step response time of more than 15 seconds had no effect and designated the sample with the reference symbol "Δ", a sample having the λ step response time of not more than 15 seconds had the effect and designated the sample with the reference symbol "O".

TABLE 3

| Sample No. | Catalyst supporting ratio (μg/mm²) Bottom part PA | Catalyst supporting ratio (μg/mm²) Leg part PB | Supporting ratio (PA/PB) | λ-point shift Amount | λ-point shift Result | 63% response characteristic Response time | 63% response characteristic Result |
|---|---|---|---|---|---|---|---|
| 14 | 30 | 35 | 0.9 | 0.0012 | Δ | 14 seconds | ○ |
| 15 | 35 | 35 | 1.0 | 0.0009 | — | 15 seconds | — |

TABLE 3-continued

| Sample No. | Catalyst supporting ratio (μg/mm²) Bottom part PA | Catalyst supporting ratio (μg/mm²) Leg part PB | Supporting ratio (PA/PB) | λ-point shift Amount | λ-point shift Result | 63% response characteristic Response time | 63% response characteristic Result |
|---|---|---|---|---|---|---|---|
| 16 | 45 | 35 | 1.3 | 0.0007 | ○ | 15 seconds | ○ |
| 17 | 55 | 35 | 1.6 | 0.0004 | Φ | 15 seconds | ○ |
| 18 | 70 | 35 | 2.0 | 0.0003 | Φ | 15 seconds | ○ |
| 19 | 80 | 35 | 2.3 | 0.0003 | Φ | 15 seconds | ○ |
| 20 | 105 | 35 | 3.0 | 0.0003 | Φ | 18 seconds | Δ |

TABLE 4

| Sample No. | Catalyst supporting ratio (μg/mm²) Bottom part PA | Catalyst supporting ratio (μg/mm²) Leg part PB | Supporting Ratio (PA/PB) ratio | λ-point shift Amount | λ-point shift Result | 63% response characteristic Response time | 63% response characteristic Result |
|---|---|---|---|---|---|---|---|
| 21 | 30 | 35 | 0.9 | 0.0011 | Δ | 14 seconds | ○ |
| 22 | 35 | 35 | 1.0 | 0.0009 | — | 15 seconds | — |
| 23 | 50 | 35 | 1.4 | 0.0008 | ○ | 15 seconds | ○ |
| 24 | 60 | 35 | 1.7 | 0.0007 | Φ | 15 seconds | ○ |
| 25 | 70 | 35 | 2.0 | 0.0006 | Φ | 15 seconds | ○ |
| 26 | 80 | 35 | 2.3 | 0.0005 | Φ | 17 seconds | Δ |

As can be understood from the experimental results show in Table 3 and Table 4, it is preferable for the supporting ratio $P_A/P_B$ of the catalyst supporting ration to have a range of not less than 1.6 and not more than 2.3 when the detection electrode in the gas sensor element has the full-surface electrode, and it is preferable for the supporting ratio $P_A/P_B$ of the catalyst supporting ration to have a range of not less than 1.7 and not more than 2.0 when the detection electrode in the gas sensor element has the partial electrode, where the electrode protection layer 160 (which is composed of the coating layer 130, the catalyst layer 140 and the poisoning layer 150) has the catalyst supporting ratio $P_A$ in the bottom part 102 and the catalyst supporting ratio $P_B$ in the leg part 101.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. A gas sensor element comprising:
   a solid electrolyte body having ion conductivity characteristics and a cylindrical shape with a bottom part;
   a reference electrode formed on an inner surface of the solid electrolyte body;
   a detection electrode formed on an outer surface of the solid electrolyte body;
   an electrode protection layer covering the outer surface of the solid electrolyte body with the detection electrode, supporting noble metal catalyst, and through which a target detection gas passes; and
   a heater inserted in the inside of the solid electrolyte body and generating heat energy when receiving electric power,
   wherein a front part of the gas sensor element has a leg part and a bottom part, the leg part is formed in parallel to an axial direction of the gas sensor element and an outer profile of a cross section of the leg part which is perpendicular to the axial direction of the gas sensor has a straight line shape, and an outer profile of a cross section of the bottom part has a curved shape,
   the detection electrode is one of a full-surface electrode and a partial electrode, the full-surface electrode is formed on the entire of the outer surface of the solid electrolyte body, and the partial electrode is formed on the leg part of and not formed on the bottom part of the outer surface of the solid electrolyte body, and
   the bottom part of the electrode protection layer has a first temperature rising speed when the heater generates heat energy, the bottom part of the electrode protection layer having the first temperature rising speed has a first quantity of noble metal catalyst, and the leg part of the electrode protection layer has a second temperature rising speed when the heater generates heat energy, and the leg part of the electrode protection layer having the second temperature rising speed has a second quantity of noble metal catalyst, and the first temperature rising speed is higher than the second temperature rising speed, and the first quantity of noble metal catalyst is larger than the second quantity of the noble metal catalyst,
   wherein the electrode protection layer has a multi layer structure composed of at least a coating layer and a catalyst layer, and the coating layer is formed so that the coating layer is in contact with the detection electrode, and the catalyst layer is formed on the coating layer, and the thickness ($T_A$) of the electrode protection layer in the bottom part is thicker than the thickness ($T_B$) of the electrode protection layer in the leg part by the catalyst layer having an increased thickness formed on the coating layer.

2. The gas sensor element according to claim 1, wherein at least one of a noble metal catalyst supporting ratio of the electrode protection layer at a boundary part between the leg part and the bottom part and a noble metal catalyst supporting ratio of the electrode protection layer in the bottom part is larger than a noble metal catalyst supporting ratio of the electrode protection layer in the leg part.

3. The gas sensor element according to claim 1, wherein the gas sensor element has a thickness ratio $T_A/T_B$ within a range of not less than 1.5 and not more than 2.5 when the detection electrode is the full-surface electrode, and the thickness ratio $T_A/T_B$ within a range of not less than 1.5 and not more than 2.0 when the detection electrode is the partial electrode, where $T_A$ is the thickness of the electrode protection layer in the bottom part and $T_B$ is the thickness of the electrode protection layer in the leg part.

4. The gas sensor element according to claim 1, wherein the gas sensor element has a supporting ratio $P_A/P_B$ within a range of not less than 1.6 and not more than 2.3 when the detection electrode is the full-surface electrode, and has the supporting ratio $P_A/P_B$ within a range of not less than 1.7 and not more than 2.0 when the detection electrode is the partial electrode, where $P_A$ is a catalyst supporting ratio of the electrode protection layer in the bottom part, and $P_B$ is a catalyst supporting ratio of the electrode protection layer in the leg part.

5. A gas sensor which detects a concentration of a specific gas contained in a target detection gas, comprising:

the gas sensor element according to claim 1;

a housing case in which the gas sensor element is placed;

an atmosphere cover case placed at a distal side of the housing case and covering the distal end part of the gas sensor element; and an element cover case placed at a front side of the gas sensor element and covering the front part of the gas sensor element.

6. The gas sensor element according to claim 1, wherein the coating layer as one layer in the multi layer structure of the electrode protection layer is directly in contact with the detection electrode, and made of metal oxide material composed of at least one of alumina, alumina magnesia spinel, and titanium, and the catalyst layer is made of metal oxide material and noble metal catalyst, where the metal oxide material is composed of at least one of alumina, alumina magnesia spinel, zirconia, and the noble metal catalyst is composed of at least one of platinum Pt, palladium Pd, rhodium Rh and ruthenium Ru.

* * * * *